United States Patent
Dalmasso

[11] Patent Number: 5,856,118
[45] Date of Patent: Jan. 5, 1999

[54] BIOLOGICAL INDICATOR AND METHOD

[76] Inventor: Joseph P. Dalmasso, P.O. Box 794, Apex, N.C. 27502

[21] Appl. No.: 9,202

[22] Filed: Jan. 20, 1998

[51] Int. Cl.$^6$ ............................... C12Q 1/22; C12Q 1/00
[52] U.S. Cl. ........................... 435/31; 435/4; 435/283.1; 435/287.4; 435/287.5; 422/50
[58] Field of Search ............................. 435/31, 4, 283.1, 435/287.4, 287.5; 422/50

[56] References Cited

U.S. PATENT DOCUMENTS

| | | | |
|---|---|---|---|
| 4,087,326 | 5/1978 | Kereluk | 435/31 |
| 4,730,726 | 3/1988 | Holzwarth | 435/31 |
| 4,756,882 | 7/1988 | Jacobs et al. | 422/50 |
| 4,777,780 | 10/1988 | Holzwarth | 435/31 |

*Primary Examiner*—Louise N. Leary
*Attorney, Agent, or Firm*—Lynn E. Barber

[57] ABSTRACT

A biological indicator including a plurality of metal carriers individually compartmentalized in a package, so that there are a plurality of different incremental population levels of a resistant test microorganism exposed at each site to test the efficacy of sterilization procedures. Preferably, the metal carriers have a surface which has been abraded, and the carriers are placed in a flat package having two parallel sides made of a material such as TYVEK™ that is permeable to, and unreactive with, the selected gas, such as $H_2O_2$.

18 Claims, 1 Drawing Sheet

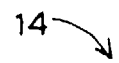
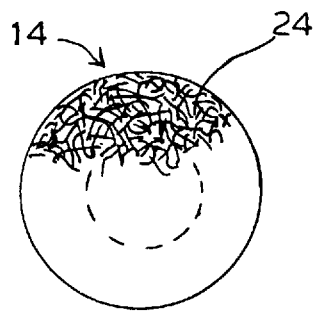
FIG. 1B    FIG. 1A
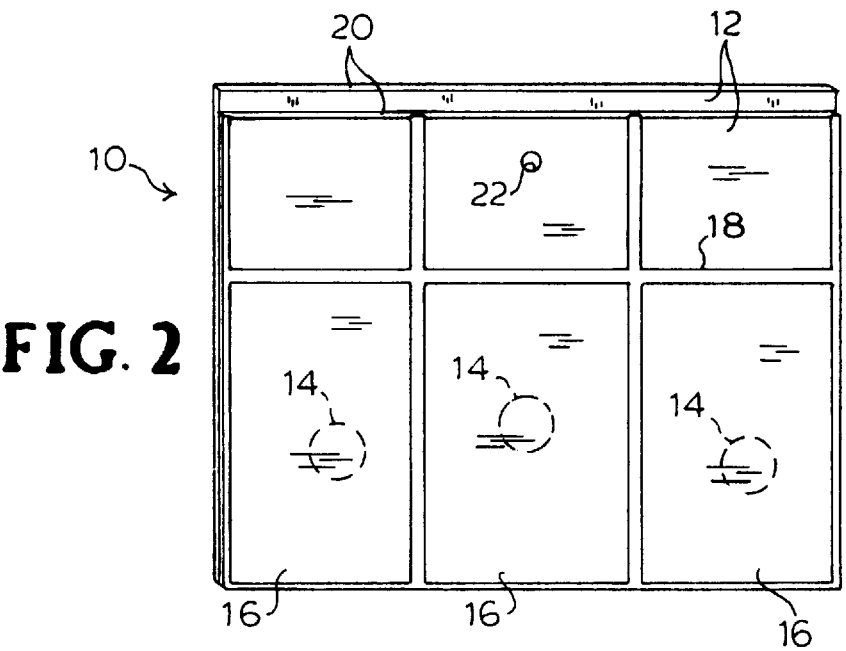
FIG. 2
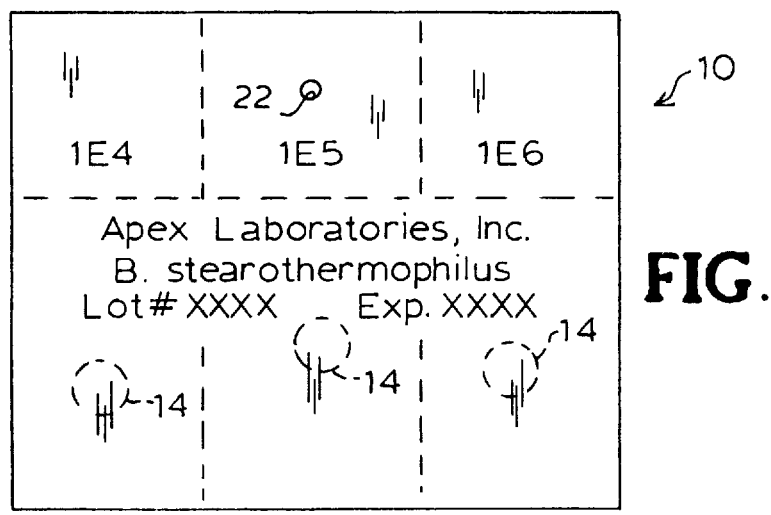
FIG. 3

BIOLOGICAL INDICATOR AND METHOD

BACKGROUND OF THE INVENTION

1. Field of the Invention

This invention relates to biological indicators, and in particular, to a biological indicator device and method for determining the effectiveness of sterilizing cycles.

2. Description of the Related Art

In the health care and related fields, there are many requirements for sterile equipment and devices. Similarly, the sterilization processes used in health care facilities and for bulk processing of medical devices can be applied to other sterilization processes, for example, the sterilization of chambers or large enclosures used in pharmaceutical sterility testing or in the processing of closed manufacturing lines requiring a sterile environment for filling pharmaceuticals.

Many traditional sterilization processes utilize steam or ethylene oxide (EtO), which both require pressure vessels in which the sterilization process takes place. With steam sterilization, the mode of action of steam and the effects of chamber materials, chamber design, and load configurations are well-understood, and present little impediment to achieving sterilization. During the straightforward killing of microorganisms in steam sterilization, the transfer of heat of vaporization from the steam, as it condenses on surfaces and microorganisms, causes thermal destruction of proteins essential for growth.

Similarly, EtO, which has been routinely used for many years, is well-understood. EtO, when introduced into a chamber, readily vaporizes and penetrates through most packaging and materials and kills by specifically reacting with alkyl groups on essential molecules. The ease of vaporization of EtO is due in large part to its high vapor pressure (760 mm Hg at 10.7° C.). EtO is also unaffected by chamber materials such as metals and paints, and packaging materials such as synthetics and cellulosics.

Although such high-pressure, high-heat sterilization processes are still widely used, there is increased use of "cold sterilization" in which sterilization is achieved at temperatures only moderately above ambient, for example, below approximately 50° C., without the need for pressure vessels as are used for steam or ethylene oxide. This process, which employs hydrogen peroxide ($H_2O_2$), is less well understood than steam sterilization, for which there are steam tables that provide the proper time and temperature parameters required to achieve sterilizing conditions in a chamber. Although not completely understood, the mechanism of kill for $H_2O_2$ is generally accepted as the action of hydroxyl (—OH) radicals produced when the hydrogen peroxide molecule reacts with critical organic and inorganic cell components. Other materials, such as divalent cations, catalysts, natural organic compounds, iron, brass, and the sharp edges of broken glass, can also cause the decomposition of $H_2O_2$ and thus cause the production of —OH radicals. Since gaseous $H_2O_2$ is reactive with many materials, each application of the technology is somewhat unique. Hydrogen peroxide is also unstable with an inherent decomposition rate in the gaseous state, which must be taken into account when using the gas for sterilization processes.

Hydrogen peroxide gas differs from the other main gaseous sterilant, EtO, in that it has a low vapor pressure (about 20 mm Hg at room temperature) under ambient conditions. Energy must be introduced to liquid $H_2O_2$ to achieve complete and rapid vaporization and reach a sterilant concentration that can be used in a timely and efficacious manner. Once produced, the $H_2O_2$ gas must be delivered to the site(s) to effect sterilization, in part due to the fragility of $H_2O_2$ and in part because the $H_2O_2$ does not readily equilibrate throughout an enclosure due to its low vapor pressure. Fans are generally used in the chamber when $H_2O_2$ gas is used to assist in the dispersion and distribution of the sterilant.

Typically biological indicators (BIs) are used for monitoring the effectiveness of a particular sterilization process or cycle. Sterilization processes used to manufacture FDA-regulated products, such as aseptically filled sterile injectables or medical devices, must be validated for efficacy, although for some steam and EtO applications, the parametric release of specific product configurations has been established. Until a broad knowledge base exists for $H_2O_2$, BIs will continue to be necessary to validate all applications.

Generally, a BI is a calibrated population of bacterial spores that are highly resistant to the mode of sterilization being monitored, which are positioned in or on a carrier that is placed in the sterilization chamber. Bacterial spores are both highly resistant to physical and chemical agents and are stable biological entities, so that a BI product utilizing spores has a long shelf life as compared to vegetative cells. *Bacillus stearothermophilus* spores have been used to monitor moist heat sterilization and gaseous hydrogen peroxide sterilization, *B. subtilis* spores have been used for ethylene oxide (EtO), dry heat sterilization, and liquid hydrogen peroxide processes, and *B. subtilis* and *B. circulans* have been used to monitor sterilization systems using peroxy compounds in the plasma state.

Biological indicators are typically used by placement of one or more BIs throughout a loaded enclosure, including placement in the most difficult to sterilize location(s), and then processing the load. After the sterilization process is complete, each BI is cultured as provided by the manufacturer in a bacteriological nutrient medium, and incubated at the appropriate temperature. The presence of growth in the medium after a suitable incubation period indicates that the sterilization process was not sufficient where the BI was positioned, while the absence of growth after a suitable incubation period indicates that acceptable sterilization conditions were achieved at the site of placement of the BI during the sterilization process.

The accepted validation method for determining the sterilization time for an enclosure is to place BIs inoculated at $1 \times 10^6$ spores per carrier through the test enclosure, conduct a partial sterilization cycle, then culture and evaluate the BIs (Steris Corporation, Mentor, Ohio, Validation Manual, VHP™ 1000 Biodecontamination System, Part No. P-129363-317, Feb. 29, 1996). The disclosure of this manual and all other publications, including patents, that are referred to herein, is incorporated herein by reference. To check the effectiveness of a particular sterilization procedure of a particular device or chamber, this process is repeated using graduated exposure times. For exposure times shorter than are required to kill $1 \times 10^6$ spores, outgrowth is complete from all such carriers. At some intermediate exposure times, there is a mix of positive and negative carriers (fractionals). An exposure time just long enough to kill $1 \times 10^6$ spores on the carriers is the desired goal, since this point is recognized as the minimum level of sterilization time acceptable for many processes. Enumerating the levels of survivors on each carrier is an alternative approach, but particularly when low numbers of viable spores remain, this method is subject to some error and potential contamination through handling, and is more labor intensive than conducting multiple fractional (survival/kill) runs.

This validation procedure of sterilization processes is readily accomplished when small chambers devoid of loads, shelves and obstructions to airflow are to be sterilized, because the $H_2O_2$ gas is easily and evenly distributed. In chambers of large size, unconventional chamber configuration, or in the presence of obstructions, however, the number of exposures needed to identify acceptable sterilization cycles may be substantially increased. Further, due to the nature of the gas and distribution difficulties, some areas of large chambers will quickly show kill, while others will require extended exposures to reach an acceptable endpoint.

Early studies using scaled sterility testing to decrease the amount of time and expense required for such testing include those reported in the patents of Kereluk (U.S. Pat. Nos. 3,711,378 and 4,087,326).

An additional problem when evaluating $H_2O_2$ systems with various cellulosic papers such as filter paper is that $H_2O_2$ readily adsorbs or absorbs to these materials and is difficult to remove. The retention of significant levels of $H_2O_2$ on such materials can lead to false negative cultures due to the continued local action of $H_2O_2$ after the gaseous sterilant source has been removed, i.e., the retained $H_2O_2$ can continue to kill spores present on the paper carrier, thus rendering a BI that normally would have been positive (shows outgrowth) to be falsely negative (shows no outgrowth). Use of metal carriers for holding the spores overcomes these problems.

It is therefore an object of this invention to reduce the time needed to test sterilization procedures by providing a biological indicator package configured to hold multiple carriers, so that there are a plurality of incremental populations of resistant test microorganisms in each package.

It is a further object of this invention to provide a biological indicator that allows accurate, rapid assessment of sterilization processes at ambient pressures, and increased spore retention on the metal carriers. Such a carrier may be useful in sub-atmospheric applications using the gaseous hydrogen peroxide technology or other gaseous peroxy sterilization systems.

Other objects and advantages will be more fully apparent from the following disclosure and appended claims.

SUMMARY OF THE INVENTION

The invention herein is for a biological indicator package comprising a plurality of metal carriers, preferably stainless steel, having a plurality of different incremental population levels of a resistant test microorganism. Preferably, the metal carriers have a surface which has been abraded, and the carriers are placed in a flat package having two parallel sides made of a material such as TYVEK™ that is permeable to, and essentially unreactive with, the sterilant gas, such as $H_2O_2$.

Other aspects and features of the invention will be more fully apparent from the following disclosure and appended claims.

BRIEF DESCRIPTION OF THE DRAWINGS

FIGS. 1A is an elevational view of a preferred carrier according to the invention herein and FIG. 1B is an upper perspective view thereof showing scuffing.

FIG. 2 is a perspective view of the front side of a package containing carriers according to the invention.

FIG. 3 is a perspective view of the back side of a package containing carriers according to the invention.

DETAILED DESCRIPTION OF THE INVENTION AND PREFERRED EMBODIMENTS THEREOF

The present invention for use in testing sterilization procedures, particularly those at ambient pressures, with a gas such as hydrogen peroxide is based on the use of specially prepared metal carriers sealed in a package that is permeable to the gas, e.g., $H_2O_2$. Although metal carriers are the preferred material described herein, plastics, composites, and ceramic materials can be made into suitable carriers using the same preparation methods employed with the metal carriers. Other gases with which the invention may also be used include chlorine dioxide, methyl bromide, and propylene oxide, to name a few. The present invention may be used for any sterilant or disinfectant gas where its efficacious properties in enclosures may not be well understood, e.g., chlorine dioxide, and in a situation where the user could benefit from minimizing the number of trial exposures to determine an appropriate exposure time. The present invention is also useful when working with toxic gases, such as methyl bromide and propylene oxide, by minimizing the number of trial exposures and thus reducing risk to the operators and speeding the overall process.

The invention provides a biological indicator package containing a plurality of carriers with a plurality of incremental levels of a test microorganism. As used herein "incremental" population levels preferably refers to ten-fold differences in the number of spores associated with different carriers, for example, carriers in a particular package may contain $1\times10^4$, $1\times10^5$, and $1\times10^6$ spores per carrier. Other incremental levels, for example, two-fold or five-fold differences between different carriers may of course be used if an increased level of accuracy is desired.

The invention enables the provision of useful information in a sterilizing chamber having a wide range of sterilant concentrations. Preferably there are at least two carriers per package, and most preferably 3–18 carriers per package, which preferably have ten-fold differences in the number of spores adhered to at least one surface of the carriers that has been abraded.

As used herein "abraded" means that at least one of the two surfaces of the preferably round carrier have been multiply scored, and most preferably refers to metal carriers having at least one side "scuffed" or abraded with an abrasive pad such as SCOTCHBRITE™ General Purpose Pad (3M, Part No. 07447) to present the metal with a visually dulled or light matte finish. This process is best accomplished by subjecting one side of the metal to the action of a rotating drum to which has been affixed SCOTCHBRITE™ pad material. Using a uniform pressure, metal stock can be pressed against the rotating pad material to impart a light scuff pattern to the metal surface.

In a modification of the present invention, individual compartments in the package may contain carriers inoculated with the same population of organisms, a process which can be useful when statistically more meaningful data are required regarding biological kill at specific site(s). An example would be a biological indicator with nine compartments, three each containing a carrier with $1\times10^2$ spores per carrier, three each with $1\times10^4$ spores per carrier, and three each with $1\times10^6$ spores per carrier.

Thus, in locations in chambers that are especially hard to reach with the sterilant gas, and that would obviously require a greater exposure time to kill all organisms, for example, in large enclosures (greater than 1000 cubic feet), there would be susceptibility of the spores on only the lower population carriers, and a concurrent survival of spores on higher population carriers. Because all carriers to be used at a single location in the area to be sterilized are packaged together, and thus are subjected to the same sterilization conditions, the conditions at a particular location can be accurately assessed with the use of one package of the invention at that location for a particular time period. Especially in large and complex installations, the time saved when conducting a validation using BIs is considerably reduced with the invention.

Preferably, *Bacillus stearothermophilus* spores are the organisms to use with gaseous hydrogen peroxide. Other bacterial endospores, which are among the most chemical and physical resistant organisms known, could be obtained from the genus Bacillus, e.g., *B. subtilis, B. cereus, B. megaterium,* etc. However, it is known that *B. stearothermophilus* shows a linear dose-response relationship to hydrogen peroxide, which makes it attractive when conducting quantitative experiments with this sterilant. See Steris Corporation, Mentor, Ohio Cycle Development Guide, VHP™ 1000 Biodecontamination System, Part No. P-129372-711, Feb. 23, 1996. Other organisms could be used, but would benefit from characterization as to their kill kinetics for this sterilant or whatever sterilant gas is used. The other attractive aspect of the genus Bacillus is that it is readily cultured in bacteriological media long used in sterility testing. The next largest genus of bacterial sporeformers, Clostridium, is composed of anaerobes, which require special growth media preparation and special handling, and thus are generally less attractive to use. Mold spores, for example, Aspergillus and Penicillium species, which are common contaminants of grains and nuts in the food industry, are another option, but generally do not uniformly exhibit the capacity to remain viable for the long periods of time preferred for biological indicators. Thus, although other organisms could be used for various sterilants, the organisms of choice generally belong to the genus Bacillus due to the ease of manufacture and ease of use by the operator.

In the most preferred embodiment, the biological indicator of the invention comprises a package 10, for example, a pouch comprising a material sufficiently permeable to the selected sterilant gas, yet functioning as a microbial barrier. The preferred material, TYVEK™, shows a Gurley porosity range of 5–100 seconds/100 cc/square inch, with a range of 8–36 seconds being the preferred value. Thus, most preferably two sheets 12 of TYVEK™ or a single folded sheet, form the parallel sides of the pouch 10. The TYVEK™ material is readily sealed by heat using an impulse sealer, heated bar sealer or any similar device. This same process is used to make the individual compartments in which uniquely inoculated carriers are placed. In the preferred embodiment of the package portion of the invention shown in FIGS. 2–3, the two sheets 12 of TYVEK™ are offset at one end (at top in FIG. 2) to allow the easier grasping of each sheet of TYVEK™ for purposes of peeling the pouch 10 open to retrieve and culture the exposed disk 14 contained within. Alternatively, the package can be cut open with scissors and the carrier disk 14 removed by tipping the pouch or by aseptic removal with forceps. In any event, the user needs to take care to remove the carrier disk 14 aseptically and place it in bacteriological growth media so that incidental microbial contaminants are not introduced that would give false positive results.

In the invention herein, the sheets of TYVEK™ are sealed or otherwise completely closed on three sides (left, right and bottom of package shown in FIG. 2) such that a larger pocket is formed, which is subdivided into a plurality of smaller pockets for holding the individual carriers. The specific inoculated indicator disks 14 are inserted into their respective pockets 16 and an additional sealing step is used to seal the pouch 10 at seal line 18 of the larger pocket. Alternatively, systems that place the disks 14 in appropriate locations on sheets of TYVEK™ and then seal a second sheet of TYVEK™ over the first, thus compartmentalizing the disks in their respective locations in one step is an optional assembly arrangement. Each package preferably is designed so that the two sheets 12 may easily be peeled apart, as is known in the art of packaging, for example by the upper edge 20 of one sheet 12 being offset from the upper edge 20 of the other sheet as shown in FIG. 2. Each pouch 10 has a means, such as a hole 22, for hanging the package in the desired spot or other means for temporarily affixing the pouch in a particular location.

The carrier disks 14 are made of a metal, for example, stainless steel or aluminum, or other metals that do affect performance of the BI. Most preferably the carriers are circles (FIG. 1B) made of grade 304 stainless steel and measure 0.35" in diameter by 0.003" thick. In this preferred embodiment, the disks have been fashioned into a dished configuration (concave on the abraded surface discussed below) to ensure that spores placed on the disk are not subject to being abraded off by the packaging as might occur with a planar disk (FIGS. 1A and 1B). The dished configuration may be made by any means known in the art, such as use of an extrusion punch having a central nominal extension so that the center of the disk is slightly stretched, forming a dish-form as shown in the figures. For a disk having a diameter of about 0.35", it has been found that a depression about 0.018" deep is adequate.

The diameter is such that the carriers can readily be placed into commercially available nutrient broth for outgrowth tests, and thus could be other sizes adapted to particular test systems, so long as they are large enough to hold the desired number of spores.

Preferably at least one surface of each metal carrier, most preferably the concave side, is abraded with a series of "scratches" 24 as diagrammatically illustrated in FIG. 1B. The hatch marks shown in the upper portion of the disk for illustration purposes in FIG. 1B indicate a scuffed surface on the dished side of the carrier. Scuff marks impart a matte or satin finish to the carrier and may not be readily apparent unless viewed under magnification. Although a simple "milled" surface as is known in the automotive field, for example, as is used for shim stock, may be used, the preferred surface is abraded by scuffing the metal with SCOTCH-BRITE™, General Purpose Pads # 07447, 3M Company, Minneapolis, Minn., as discussed below in more detail in Example 1. Abrasion of the carriers enhances the adherence of the spores to the metal surface, as shown in the Examples.

Each carrier is inoculated at a selected level of spores on the abraded side (spores not shown in Figures due to the microscopic size of spores), for example, there might be a first carrier having $1 \times 10^6$ spores, another having $1 \times 10^5$ spores, another having $1 \times 10^4$ spores, etc. Thus, the level of spores on the different carriers varies, preferably by a factor of 10 or more. The means of inoculation of the carriers is via a calibrated pipetting device or other method that delivers uniform quantities of inoculum to each carrier. The suspension being inoculated is prepared in general by growing organisms on semi-solid nutrient agar under the appropriate conditions and for a period of time to permit the production of spores, as is known in the art. The spores are harvested using generally aqueous solutions and cleaned of excess cellular debris by standard methods of centrifugation. The spores are preferably suspended in water or dilute ethanol diluents, but may be suspended in wide variety of solutions so long as the viability and resistance properties of the spores are not compromised.

The biological indicator of the invention is preferably used by a person experienced in the validation of chambers or enclosures and with the specific sterilant.

The features and advantages of the present invention will be more clearly understood by reference to the following examples, which are not to be construed as limiting the invention.

EXAMPLES

EXAMPLE 1—Comparison of Carriers Prepared According to the Invention with Non-Abraded Metal Carriers Samples of carrier material consisting of 1⅜" wide× approximately 24" long×0.003" thick grade 304 stainless steel having a 2B finish are divided into two lots. One lot is scuffed with SCOTCH-BRITE™ general purpose pad (Part No. 07447) attached to a rotating drum. The material is lightly abraded by pressing against the rotating pad until a slightly dull or matte finish is achieved, which under magnification appears as a lightly and uniformly scratched surface. The other lot is not treated. The two lots of stainless steel are used to prepare disks, 0.35" in diameter. The disks are punched with a tool that results in a 0.018" dish-shaped depression in each disk. Both lots are cleaned with 95% ethanol to remove surface dirt and sterilized in a hot air oven for two hours at 160° C. Aliquots of 20 $\mu$l of bacterial spores, containing nominally $6\times10^6$ spores are respectively inoculated on to each carrier using a calibrated 20 $\mu$l pipette (Rainin) and allowed to dry overnight under ambient conditions. The two lots of carriers are then placed in respective petri dishes and the lids replaced. The two dishes, one containing inoculated carriers, and one containing uninoculated carriers, are held together and shaken vigorously for 8–10 seconds in a reciprocal motion to identically simulate mechanical conditions that would occur during shipping. Carriers are then individually placed in known volumes of diluent, sonicated for 30 minutes to remove residual spores, heat shocked, serially diluted and enumerated using accepted methodology (USP XXII, 1995. Official Monograph, Biological Indicator for Steam Sterilization: Paper Strip). Results are shown in Table 1.

TABLE 1

| Sample Description | CFU* per carrier (average of two plates) |
|---|---|
| Test (abraded) | $5.7 \times 10^6$ |
|  | $6.3 \times 10^6$ |
|  | $5.8 \times 10^6$ |
|  | $4.0 \times 10^6$ |
| Average of 4 samples | $5.4 \times 10^6$ |
| Control (not abraded) | $3.7 \times 10^4$ |
|  | $3.2 \times 10^4$ |
|  | $3.57 \times 10^4$ |
|  | $3.97 \times 10^4$ |
| Average of 4 samples | $3.67 \times 10^4$ |

*Number of colony-forming units

EXAMPLE 2—Use of Carriers at One Inoculum Level in a Sterilizing Cycle

A number of metal carriers are prepared with scuffing according to Example 1 using a SCOTCH-BRITE™ general-purpose pad. After sterilizing by exposing to dry heat at 160° C. for three hours, each metal carrier is inoculated with a selected number of Bacillus stearothermophilus spores, as follows: using a 20 $\mu$l calibrated pipette, dispense 20 $\mu$l volumes containing nominally $2\times10^6$ spores onto each carrier. The carriers are placed in a laminar flow hood and allowed to dry for two hours at ambient conditions. The inoculated metal carriers are placed in a package consisting of two sheets of TYVEK™ that are sealed so as to contain a plurality of carriers, each individually placed in a compartment sealed on all four sides. The prepared carriers are positioned at varying locations in a 32 cubic foot pharmaceutical rigid-walled isolator, exposed to gaseous $H_2O_2$ for 30 minutes, and then are aseptically transferred to tubes of soybean casein digest broth (Accumedia Manufacturers, Inc. Baltimore, Md.). See USP XXIII, 1995. Microbiological Tests: 71, Sterility Tests. The tubes are placed in an incubator at 57.5°±2.5° C. and incubated for seven days. At the end of seven days, all carriers are examined and found to be negative, indicating that sufficient sterilization has occurred. Control carriers which are not exposed to sterilant, but are cultured under identical conditions, are positive (outgrowth occurs).

EXAMPLE 3—Use of Incrementally Inoculated Carriers of the Invention in an Enclosed Chamber An indicator package of TYVEK™ is prepared according to the present invention having six carriers, comprising a series of carriers having different levels of spores, so that each carrier has ten-fold more spores than the next lowest level carrier. Thus the six carriers to be placed at each location have $1\times10^1$, $1\times10^2$, $1\times10^3$, $1\times10^4$, $1\times10^5$, and $1\times10^6$ spores per carrier, respectively. An operator decides for a particular sterilizing process to conduct an initial exposure time of two hours. As known to one of skill in the art, indicators are minimally placed in all corners of an enclosure and at the surface of the geometric centers of all walls, the floor and the ceiling of the enclosure. These areas are among those least likely to have sterilant readily delivered during an exposure cycle. Several indicators are placed in the general area of the enclosure that is the farthest from the sterilant inlet. Indicators are also placed in areas where circulating fans are likely to have poor delivery or mixing of sterilant gas. If shelves, containers, apparatus, equipment, or other obstructions are in the enclosure, the operator, from experience, estimates locations where sterilant gas is least likely to penetrate and at a minimum places indicators in those locations. The operator then initiates a sterilization cycle of a sufficient length of time, which in this example is two hours with hydrogen peroxide, based on an estimate of the efficiency of the particular gas distribution system. At the end of the cycle, the operator collects, labels and individually cultures respective indicators in an appropriate bacteriological nutrient broth. After a suitable period of incubation, which can vary from 2–14 days but is generally 7 days, the operator observes to see if there is outgrowth of specific carriers at each site. In other words, the carriers which resulted in growth at each location are determined. For any locations where all carriers, including the $1\times10^6$ carrier are negative, the exposure time is deemed to have been adequate to achieve the reduction of $1\times10^6$ resistant spores. For a location that shows the $1\times10^1$, $1\times10^2$, $1\times10^3$, $1\times10^4$ carriers are negative while the $1\times10^5$ and $1\times10^6$ carriers are positive, the user can determine that the selected exposure time is inadequate and must be extended. For this specific site, the appropriate exposure time to kill $1\times10^6$ spores can be estimated to be approximately 3 hours. Such estimated exposure times can be calculated by using the method of Stumbo (Stumbo, C. R., 1973. *Thermobacteriology in Food Processing*. 2nd Ed. New York, Academic Press).

At another specific site in the same enclosure as discussed above, where the $1\times10^1$ and $1\times10^2$ carriers are negative and the $1\times10^3$, $1\times10^4$, $1\times10^5$, and $1\times10^6$ carriers are positive, it is apparent that this location has been exposed to lower levels of sterilant gas, i.e., sufficient gas to kill populations of $1\times10^1$ and $1\times10^2$ but not to kill $1\times10^3$ and greater populations. In this example, this is now the worst case location in the enclosure, and the user can estimate that the exposure time require to kill $1\times10^6$ spores at the latter site would be approximately 6 hours. Again, a more accurate estimate can be calculated using the method of Stumbo. Thus, using the invention herein, with a single exposure time, the operator can estimate closely the required time to kill $1\times10^6$ spores at the most difficult to sterilize site. Simultaneously, the operator can readily identify the site that is most problematic with respect to delivering adequate levels of sterilant gas. A second validation run to ascertain the accuracy of the newly calculated exposure is preferred. If the results of the second run are acceptable, the operator, as is normal in the industry, conducts three successive sterilization runs using minimally $1\times10^6$ inoculated carriers and demonstrates kill on carriers placed in all locations.

The operator in the methods prior to the invention, using carriers with $1\times10^6$ spores, would have observed multiple positive carriers (carriers with remaining viable spores) with the invention at the two-hour exposure time. If the operator's estimate for the required exposure time indicated that the time should be doubled to four hours, there still would have been multiple positive carriers, but in fewer locations. If the operator's estimate then doubled the exposure time again to eight hours, there would have been no positive carriers. Since the objective in the manufacturing equipment environment is to determine the approximate exposure time when $1\times10^6$ spores are killed, thus permitting optimal manufacturing scheduling and throughput, the operator would then necessarily have needed to test a lower exposure time, e.g., 7 hours. According to this example, all carriers would have been negative at seven hours exposure, necessitating testing at another reduced time, e.g., 6 hours. Depending on the skill of the operator, several additional runs would be needed with the prior method, to confirm that the 6-hour time point is that which just killed all carriers containing $1\times10^6$ spores.

It is evident from the above example that the prior alternative to validating a particular chamber requires considerably more runs than are necessary for the invention herein, depending on the skill and experience of the operator. Thus, the invention herein saves considerable time for the user 1) by requiring that fewer test runs be conducted to estimate quickly the correct exposure time to kill $1\times10^6$ spores; and 2) by eliminating the extended culturing and incubation times following each exposure run to permit the carriers to demonstrate whether outgrowth will occur. Further, use of the invention herein permits those less skilled in the art of validation to conduct such processes with a reasonable degree of efficiency.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A biological indicator for use in sterilizing with a selected sterilant gas, comprising:
    (a) a package that is permeable to the sterilant gas; and
    (b) a plurality of metal carriers located within the package, each of the carriers having at least one abraded surface, and each of the carriers having a number of spores adhering to the at least one abraded surface of the carrier, wherein the number of spores on the carriers varies incrementally between carriers.

2. The biological indicator of claim 1, wherein the package is formed with individual compartments, each of which compartments contains a metal carrier.

3. The biological indicator of claim 1, wherein the package has two parallel sides.

4. The biological indicator of claim 3, wherein the package is made of is TYVEK™.

5. The biological indicator of claim 4, wherein the package is formed with individual compartments, each of which compartments contains a metal carrier.

6. The biological indicator of claim 1 wherein the gas is selected from the group consisting of hydrogen peroxide, chlorine dioxide, methyl bromide, and propylene oxide.

7. The biological indicator of claim 6, wherein the gas is hydrogen peroxide.

8. The biological indicator of claim 1, wherein the abraded surface is formed by treating with an abrasive material to cause the surface to be scuffed.

9. The biological indicator of claim 1, wherein each of the metal carriers is centrally concave on the abraded surface.

10. A method of determining efficacy of a sterilization process at a sterilization site with a selected sterilant gas, comprising:
    (a) providing a biological indicator, comprising:
        (i) a package that is permeable to the sterilant gas; and
        (ii) a plurality of metal carriers located within the package, each of the carriers having at least one abraded surface, and each of the carriers having a number of spores adhering to the at least one abraded surface of the carrier, wherein the number of spores on the carriers varies incrementally between carriers; and
    (b) placing a plurality of packages of the biological indicator at selected locations within the sterilization site.

11. The method of claim 10, wherein the package is formed with individual compartments, each of which compartments contains a metal carrier.

12. The method of claim 10, wherein the package has two parallel sides.

13. The method of claim 12, wherein the package is made of TYVEK™ and the selected sterilant gas is hydrogen peroxide.

14. The method of claim 13, wherein the package is formed with individual compartments, each of which compartments contains a metal carrier.

15. The method of claim 10 wherein the gas is selected from the group consisting of hydrogen peroxide, chlorine dioxide, methyl bromide, and propylene oxide.

16. The method of claim 15, wherein the gas is hydrogen peroxide.

17. The method of claim 10, wherein the abraded surface is formed by treating with an abrasive material to cause the surface to be scuffed.

18. The method of claim 1, wherein each of the metal carriers is centrally concave on the abraded surface.

* * * * *